(12) United States Patent
Collins

(10) Patent No.: US 7,822,485 B2
(45) Date of Patent: Oct. 26, 2010

(54) METHOD AND APPARATUS FOR SPINAL COOLING

(75) Inventor: Kenneth A. Collins, Mission Viejo, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 993 days.

(21) Appl. No.: 11/527,332

(22) Filed: Sep. 25, 2006

(65) Prior Publication Data

US 2008/0077206 A1   Mar. 27, 2008

(51) Int. Cl.
*A61F 7/12* (2006.01)
*A61F 7/00* (2006.01)

(52) U.S. Cl. .................... 607/117; 607/105; 607/113

(58) Field of Classification Search ............ 606/93; 607/105, 113, 117
See application file for complete search history.

(56) References Cited

U.S. PATENT DOCUMENTS

| | | | | |
|---|---|---|---|---|
| 4,904,237 A * | 2/1990 | Janese | .......... | 604/28 |
| 5,207,640 A | 5/1993 | Hattler | .......... | 604/28 |
| 5,230,862 A | 7/1993 | Berry et al. | .......... | 422/48 |
| 5,271,743 A | 12/1993 | Hattler | .......... | 604/26 |
| 5,450,516 A | 9/1995 | Pasquali et al. | .......... | 385/115 |
| 5,470,659 A | 11/1995 | Baumgart et al. | .......... | 428/398 |
| 5,725,949 A | 3/1998 | Pasquali et al. | .......... | 428/398 |
| 5,730,754 A * | 3/1998 | Obenchain | .......... | 606/185 |
| 5,735,809 A | 4/1998 | Gorsuch | .......... | 428/364 |
| 5,741,261 A * | 4/1998 | Moskovitz et al. | .......... | 606/79 |
| 5,755,690 A | 5/1998 | Saab | .......... | 604/96 |
| 5,772,661 A * | 6/1998 | Michelson | .......... | 606/86 A |
| 5,837,003 A | 11/1998 | Ginsburg | .......... | 607/106 |
| 5,876,667 A | 3/1999 | Gremel et al. | .......... | 604/4 |
| 5,879,329 A | 3/1999 | Ginsburg | .......... | 604/93 |
| 5,879,371 A * | 3/1999 | Gardiner et al. | .......... | 606/224 |
| 5,885,291 A * | 3/1999 | Moskovitz et al. | .......... | 606/79 |
| 5,989,238 A | 11/1999 | Ginsburg | .......... | 604/93 |
| 6,004,289 A | 12/1999 | Saab | .......... | 604/96 |
| 6,019,783 A | 2/2000 | Philips | .......... | 607/105 |
| 6,042,559 A | 3/2000 | Dobak | .......... | 604/7 |
| 6,074,401 A * | 6/2000 | Gardiner et al. | .......... | 606/139 |
| 6,096,068 A | 8/2000 | Dobak | .......... | 607/105 |
| 6,110,168 A | 8/2000 | Ginsburg | .......... | 606/27 |
| 6,126,684 A | 10/2000 | Gobin | .......... | 607/113 |
| 6,146,411 A | 11/2000 | Noda | .......... | 607/105 |
| 6,149,658 A * | 11/2000 | Gardiner et al. | .......... | 606/139 |
| 6,149,670 A | 11/2000 | Worthen | .......... | 607/3 |
| 6,149,673 A | 11/2000 | Ginsburg | .......... | 647/96 |
| 6,149,676 A | 11/2000 | Ginsburg | .......... | 607/106 |
| 6,149,677 A | 11/2000 | Dobak | .......... | 607/106 |
| 6,165,207 A | 12/2000 | Balding | .......... | 607/105 |

(Continued)

FOREIGN PATENT DOCUMENTS

WO    2006023056    3/2006

(Continued)

*Primary Examiner*—Roy D Gibson
*Assistant Examiner*—Kaitlyn E Helling
(74) *Attorney, Agent, or Firm*—John L. Rogitz

(57) ABSTRACT

A method for exchanging heat with a patient's spinal column incident to spinal surgery or to relieve a patient for a hypoxia condition of the spine. A closed loop heat exchange catheter is percutaneously advanced into the retroperitoneal space of the patient, and then heat exchange fluid is circulated through the catheter to cool the spinal column.

3 Claims, 1 Drawing Sheet

U.S. PATENT DOCUMENTS

| | | | |
|---|---|---|---|
| 6,210,412 B1 * | 4/2001 | Michelson | 606/86 A |
| 6,217,552 B1 * | 4/2001 | Barbut et al. | 604/113 |
| 6,224,624 B1 | 5/2001 | Lasheras | 607/105 |
| 6,231,594 B1 | 5/2001 | Dae | 607/96 |
| 6,231,595 B1 | 5/2001 | Dobak | 607/106 |
| 6,235,048 B1 | 5/2001 | Dobak | 607/104 |
| 6,238,428 B1 | 5/2001 | Werneth | 607/105 |
| 6,245,095 B1 | 6/2001 | Dobak | 607/105 |
| 6,251,129 B1 | 6/2001 | Dobak | 607/105 |
| 6,251,130 B1 | 6/2001 | Dobak | 607/105 |
| 6,254,626 B1 | 7/2001 | Dobak | 607/105 |
| 6,264,679 B1 | 7/2001 | Keller | 607/105 |
| 6,287,326 B1 | 9/2001 | Pecor | 607/105 |
| 6,290,717 B1 | 9/2001 | Philips | 607/113 |
| 6,299,599 B1 | 10/2001 | Pham | 604/113 |
| 6,306,161 B1 | 10/2001 | Ginsburg | 607/106 |
| 6,312,452 B1 | 11/2001 | Dobak | 607/105 |
| 6,325,818 B1 | 12/2001 | Werneth | 607/105 |
| 6,338,727 B1 | 1/2002 | Noda | 604/113 |
| 6,342,074 B1 * | 1/2002 | Simpson | 623/17.11 |
| 6,364,899 B1 | 4/2002 | Dobak | 607/113 |
| 6,368,304 B1 | 4/2002 | Aliberto | 604/113 |
| 6,379,331 B2 * | 4/2002 | Barbut et al. | 604/113 |
| 6,379,378 B1 | 4/2002 | Werneth | 607/96 |
| 6,383,210 B1 | 5/2002 | Magers | 607/105 |
| 6,393,320 B2 | 5/2002 | Lasersohn | 607/3 |
| 6,405,080 B1 | 6/2002 | Lasersohn | 607/3 |
| 6,409,747 B1 | 6/2002 | Gobin | 607/113 |
| 6,416,533 B1 | 7/2002 | Gobin | 607/113 |
| 6,419,643 B1 | 7/2002 | Shimada | 600/323 |
| 6,428,563 B1 | 8/2002 | Keller | 607/105 |
| 6,432,124 B1 | 8/2002 | Worthen | 607/105 |
| 6,436,130 B1 | 8/2002 | Philips | 607/105 |
| 6,436,131 B1 | 8/2002 | Ginsburg | 607/106 |
| 6,440,158 B1 | 8/2002 | Saab | 604/105 |
| 6,447,474 B1 | 9/2002 | Balding | 604/66 |
| 6,450,987 B1 | 9/2002 | Kramer | 604/523 |
| 6,450,990 B1 | 9/2002 | Walker | 604/113 |
| 6,451,045 B1 | 9/2002 | Walker | 607/105 |
| 6,454,792 B1 | 9/2002 | Noda | 607/105 |
| 6,454,793 B1 | 9/2002 | Evans | 607/105 |
| 6,458,150 B1 | 10/2002 | Evans | 607/105 |
| 6,460,544 B1 | 10/2002 | Worthen | 607/105 |
| 6,464,716 B1 | 10/2002 | Dobak | 607/105 |
| 6,468,296 B1 | 10/2002 | Dobak | 607/105 |
| 6,471,717 B1 | 10/2002 | Dobak | 607/105 |
| 6,475,231 B2 | 11/2002 | Dobak | 607/105 |
| 6,478,811 B1 | 11/2002 | Dobak | 607/105 |
| 6,478,812 B2 | 11/2002 | Dobak | 607/105 |
| 6,482,226 B1 | 11/2002 | Dobak | 607/104 |
| 6,491,039 B1 | 12/2002 | Dobak | 128/898 |
| 6,491,716 B2 | 12/2002 | Dobak | 607/105 |
| 6,494,903 B2 | 12/2002 | Pecor | 607/105 |
| 6,497,721 B2 | 12/2002 | Ginsburg | 607/106 |
| 6,516,224 B2 | 2/2003 | Lasersohn | 607/3 |
| 6,520,933 B1 | 2/2003 | Evans | 604/103.07 |
| 6,527,798 B2 * | 3/2003 | Ginsburg et al. | 607/106 |
| 6,529,775 B2 | 3/2003 | Whitebook | 607/100 |
| 6,530,946 B1 | 3/2003 | Noda | 607/113 |
| 6,533,804 B2 | 3/2003 | Dobak | 607/105 |
| 6,540,771 B2 | 4/2003 | Dobak | 607/105 |
| 6,544,282 B1 | 4/2003 | Dae | 607/105 |
| 6,551,349 B2 | 4/2003 | Lasheras | 607/105 |
| 6,554,797 B1 | 4/2003 | Worthen | 604/113 |
| 6,558,412 B2 | 5/2003 | Dobak | 607/105 |
| 6,572,538 B2 | 6/2003 | Takase | 600/140 |
| 6,572,638 B1 | 6/2003 | Dae et al. | 607/96 |
| 6,572,640 B1 | 6/2003 | Balding | 607/105 |
| 6,576,001 B2 | 6/2003 | Werneth | 607/96 |
| 6,576,002 B2 | 6/2003 | Dobak | 607/105 |
| 6,581,403 B2 | 6/2003 | Whitebook | 62/434 |
| 6,582,398 B1 | 6/2003 | Worthen | 604/113 |
| 6,582,455 B1 | 6/2003 | Dobak | 607/105 |
| 6,582,457 B2 | 6/2003 | Dae | 607/113 |
| 6,585,692 B1 | 7/2003 | Worthen | 604/113 |
| 6,585,752 B2 | 7/2003 | Dobak | 607/105 |
| 6,589,271 B1 | 7/2003 | Tzeng | 607/113 |
| 6,595,967 B2 | 7/2003 | Kramer | 604/523 |
| 6,599,312 B2 | 7/2003 | Dobak | 607/105 |
| 6,602,243 B2 | 8/2003 | Noda | 604/544 |
| 6,602,276 B2 | 8/2003 | Dobak | 607/105 |
| 6,607,517 B1 | 8/2003 | Dae | 604/31 |
| 6,610,083 B2 | 8/2003 | Keller | 607/105 |
| 6,620,130 B1 | 9/2003 | Ginsburg | 604/113 |
| 6,620,131 B2 | 9/2003 | Pham | 604/113 |
| 6,620,188 B1 | 9/2003 | Ginsburg | 607/106 |
| 6,620,189 B1 | 9/2003 | MacHold et al. | 607/106 |
| 6,623,516 B2 | 9/2003 | Saab | 607/105 |
| 6,635,076 B1 | 10/2003 | Ginsburg | 607/106 |
| 6,641,602 B2 | 11/2003 | Balding | 607/105 |
| 6,641,603 B2 | 11/2003 | Walker | 607/105 |
| 6,645,234 B2 | 11/2003 | Evans | 607/113 |
| 6,648,906 B2 | 11/2003 | Lasheras | 607/105 |
| 6,648,908 B2 | 11/2003 | Dobak | 607/105 |
| 6,652,565 B1 | 11/2003 | Shimada | 607/113 |
| 6,656,209 B1 | 12/2003 | Ginsburg | 607/106 |
| 6,660,028 B2 | 12/2003 | Magers | 607/105 |
| 6,673,098 B1 | 1/2004 | MacHold | 607/106 |
| 6,676,688 B2 | 1/2004 | Dobak | 607/105 |
| 6,676,689 B2 | 1/2004 | Dobak | 607/105 |
| 6,676,690 B2 | 1/2004 | Werneth | 607/105 |
| 6,679,906 B2 | 1/2004 | Hammack | 607/105 |
| 6,679,907 B2 | 1/2004 | Dobak | 607/105 |
| 6,682,551 B1 | 1/2004 | Worthen | 607/105 |
| 6,685,732 B2 | 2/2004 | Kramer | 607/106 |
| 6,685,733 B1 | 2/2004 | Dae | 607/105 |
| 6,692,488 B2 | 2/2004 | Dobak | 606/21 |
| 6,692,519 B1 | 2/2004 | Hayes | 607/105 |
| 6,695,873 B2 | 2/2004 | Dobak | 607/105 |
| 6,695,874 B2 | 2/2004 | MacHold | 607/106 |
| 6,699,268 B2 | 3/2004 | Kordis | 607/113 |
| 6,699,269 B2 * | 3/2004 | Khanna | 607/105 |
| 6,702,783 B1 | 3/2004 | Dae | 604/113 |
| 6,702,839 B1 | 3/2004 | Dae | 607/96 |
| 6,702,840 B2 | 3/2004 | Keller | 607/105 |
| 6,702,841 B2 | 3/2004 | Nest | 607/105 |
| 6,702,842 B2 | 3/2004 | Dobak | 607/105 |
| 6,706,060 B2 | 3/2004 | Tzeng | 607/105 |
| 6,709,448 B2 | 3/2004 | Walker | 607/105 |
| 6,716,188 B2 | 4/2004 | Noda | 604/6.13 |
| 6,716,236 B1 | 4/2004 | Tzeng | 607/113 |
| 6,719,723 B2 | 4/2004 | Werneth | 604/113 |
| 6,719,724 B1 | 4/2004 | Walker | 604/113 |
| 6,719,779 B2 | 4/2004 | Daoud | 607/105 |
| 6,726,653 B2 | 4/2004 | Noda | 604/113 |
| 6,726,708 B2 | 4/2004 | Lasheras | 607/105 |
| 6,726,710 B2 | 4/2004 | Worthen | 607/105 |
| 6,733,517 B1 | 5/2004 | Collins | 607/105 |
| 6,740,109 B2 | 5/2004 | Dobak | 607/105 |
| 6,749,585 B2 | 6/2004 | Aliberto | 604/113 |
| 6,749,625 B2 | 6/2004 | Pompa | 607/105 |
| 6,752,786 B2 | 6/2004 | Callister | 604/113 |
| 6,755,850 B2 | 6/2004 | Dobak | 607/104 |
| 6,755,851 B2 | 6/2004 | Noda | 607/113 |
| 6,913,607 B2 * | 7/2005 | Ainsworth et al. | 606/151 |
| 2001/0007951 A1 | 7/2001 | Dobak | 607/106 |
| 2001/0016764 A1 | 8/2001 | Dobak, III | 607/105 |
| 2001/0018539 A1 * | 8/2001 | Huang et al. | 560/139 |
| 2001/0041923 A1 | 11/2001 | Dobak | 607/105 |
| 2001/0049527 A1 * | 12/2001 | Cragg | 606/61 |
| 2002/0007203 A1 | 1/2002 | Gilmartin | 607/105 |
| 2002/0016621 A1 | 2/2002 | Werneth | 607/96 |
| 2002/0068964 A1 | 6/2002 | Dobak | 607/113 |
| 2002/0077680 A1 | 6/2002 | Noda | 600/549 |

| | | | | | |
|---|---|---|---|---|---|
| 2002/0091390 A1* | 7/2002 | Michelson ............... 606/61 |
| 2002/0091429 A1 | 7/2002 | Dobak ............... 607/105 |
| 2002/0111616 A1 | 8/2002 | Dea ............... 606/27 |
| 2002/0151946 A1 | 10/2002 | Dobak, III ............... 607/105 |
| 2002/0173803 A1* | 11/2002 | Ainsworth et al. ............... 606/151 |
| 2002/0177804 A1 | 11/2002 | Saab ............... 607/105 |
| 2002/0183692 A1 | 12/2002 | Callister ............... 604/113 |
| 2002/0193738 A1 | 12/2002 | Adzich ............... 604/113 |
| 2002/0193853 A1 | 12/2002 | Worthen ............... 607/3 |
| 2002/0193854 A1 | 12/2002 | Dobak ............... 607/105 |
| 2002/0198579 A1* | 12/2002 | Khanna ............... 607/105 |
| 2003/0078641 A1 | 4/2003 | Dobak ............... 607/105 |
| 2003/0114835 A1 | 6/2003 | Noda ............... 604/544 |
| 2003/0144714 A1 | 7/2003 | Dobak ............... 607/104 |
| 2003/0187489 A1 | 10/2003 | Dobak ............... 607/105 |
| 2003/0195465 A1 | 10/2003 | Worthen ............... 604/113 |
| 2003/0195466 A1 | 10/2003 | Pham ............... 604/113 |
| 2003/0195597 A1 | 10/2003 | Keller ............... 607/105 |
| 2003/0216799 A1 | 11/2003 | Wortheu ............... 606/27 |
| 2004/0044388 A1 | 3/2004 | Pham ............... 607/105 |
| 2004/0087934 A1 | 5/2004 | Dobak |
| 2004/0102825 A1 | 5/2004 | Daoud |
| 2004/0102826 A1 | 5/2004 | Lasheras |
| 2004/0102827 A1 | 5/2004 | Werneth |
| 2004/0106969 A1 | 6/2004 | Dobak |
| 2004/0116987 A1 | 6/2004 | Magers |
| 2004/0116988 A1 | 6/2004 | Hammack |
| 2004/0127851 A1 | 7/2004 | Noda ............... 604/503 |
| 2004/0210231 A1 | 10/2004 | Boucher et al. |
| 2004/0249465 A1* | 12/2004 | Ferree ............... 623/17.16 |
| 2006/0036302 A1* | 2/2006 | Kasza et al. ............... 607/105 |
| 2009/0198283 A1* | 8/2009 | Morgan et al. ............... 606/279 |

FOREIGN PATENT DOCUMENTS

WO    WO 2006/023056     3/2006

* cited by examiner

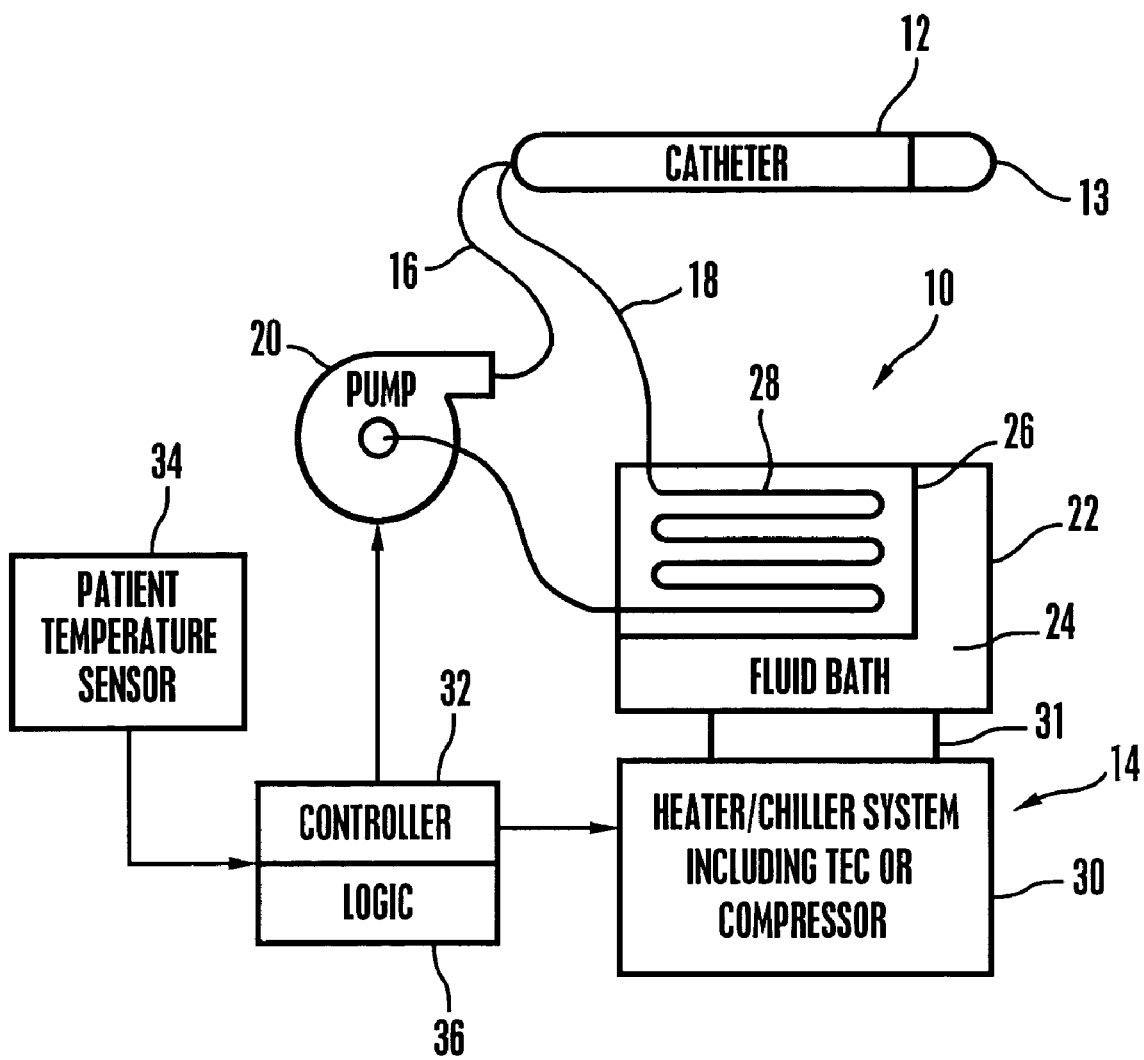
Figure 1
Figure 2
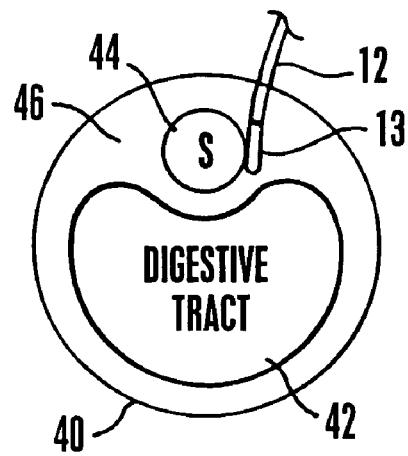

METHOD AND APPARATUS FOR SPINAL COOLING

FIELD OF THE INVENTION

The present invention relates generally to methods and apparatus for exchanging heat with the spine of a patient.

BACKGROUND OF THE INVENTION

It has been discovered that the medical outcome for a patient suffering from various maladies, e.g., severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as spinal surgery or to counter the effects of spinal injury, the present invention recognizes that cooling the spine can be advantageous.

The following U.S. patents, all of which are incorporated herein by reference, disclose various intravascular catheters/systems/methods which, as understood herein, can be used in the novel non-intravascular approach described herein: U.S. Pat. Nos. 6,749,625, 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, and U.S. patent application Ser. No. 10/355,776.

SUMMARY OF THE INVENTION

A method for treating a patient includes instructing a medical caregiver to advance a closed loop heat exchange catheter into the retroperitoneal space of the patient, and to circulate heat exchange fluid through the catheter. The instructions may be given by, e.g., a medical device manufacturer as part of regulatory labeling.

The catheter may be advanced percutaneously into the patient, and in preferred implementations the heat exchange fluid is colder than the patient. The catheter is closed loop in that heat exchange fluid does not exit the catheter into the patient.

Preferably, a heat exchange element of the catheter is positioned against the spinal column. The heat exchange element can be spiral shaped, it can be plastic or metal, and/or it can be a balloon.

In another aspect, a method for cooling at least a portion of a spinal column of a patient disposed in an operating room includes advancing a closed loop heat exchange catheter into the retroperitoneal space of the patient, and circulating heat exchange fluid through the catheter to cool the spinal column. Spinal surgery is then conducted on the patient.

In another aspect, a method for treating a patient for a hypoxia condition of the spine includes advancing a closed loop heat exchange catheter into the retroperitoneal space of the patient, and circulating heat exchange fluid through the catheter to cool the spinal column and thereby relieve the patient of at least some deleterious effects of spinal hypoxia. The hypoxia condition may be caused by cardiac arrest, myocardial infarction, stroke, or trauma.

The details of the present invention, both as to its construction and operation, can best be understood in reference to the accompanying drawings, in which like numerals refer to like parts, and which:

BRIEF DESCRIPTION OF THE DRAWINGS

FIG. 1 is a block diagram of an exemplary patient cooling system; and

FIG. 2 is a cross-section of a patient, showing the retroperitoneal space and the catheter placed therein.

DETAILED DESCRIPTION OF THE PREFERRED EMBODIMENT

Referring initially to FIG. 1, a patient heat exchange system is shown and generally designated 10. The system 10 includes an indwelling heat exchange catheter 12 that can be inserted into a patient to heat or cool the patient. The catheter 12 may be any of the catheters disclosed in the above-referenced patents or other appropriate closed loop heat exchange catheters.

Coolant such as but not limited to saline is circulated through the catheter 12 in a closed loop to and from a member such as a heat exchange system 14 through coolant supply and return tubes 16, 18 under the influence of a pump 20 (such as but not limited to a gear pump, roller pump, diaphragm pump, or other type of pump) to heat or cool the coolant as desired to warm or cool a patient. The catheter 12 is made of biocompatible material that may be coated with an anti-coagulant substance such as Heperin®. Preferably, the catheter 12 is made of flexible plastic, and on its distal end it may include one or more heat exchange elements 13 such as balloons or fibers (including intertwined spiral balloons) or metallic structures.

In the particular non-limiting embodiment shown in FIG. 1, the cooling system 14 includes a working fluid bath container 22 in which a working fluid bath 24 such as saline, glycol, a mixture thereof, or other appropriate working fluid is disposed. The container 22 may define a cooling receptacle 26 that can receive a tubing set 28 through which coolant flows as part of the closed coolant path. The tubing set 28 may be implemented as a single length of IV tubing or, as indicated in FIG. 1, the tubing set 28 may include a serpentine-like coolant path in a bag-like cartridge assembly that can be easily engaged and disengaged with the receptacle 26. In any case, it will be appreciated that the working fluid in the bath 24 is in thermal contact with the cooling receptacle 26 and, hence, with the coolant in the tubing set 28 to cool the patient coolant flowing through the path when the patient coolant is warmer than the working fluid.

The cooling system 14 also includes a heat sink 30 that is in thermal contact with the working fluid in the bath 24. The working fluid may be circulated between the heat sink 30 and the bath 24. The heat sink 30 may be a combined heater/chiller system that can include a refrigerant compressor and/or a thermo-electric cooler (TEC) to cool working fluid. Details of various types of non-limiting heat sinks are set forth in selected of the above-referenced U.S. patents. In any case, a thermal interface 31 can be provided in some implementations to permit heat transfer between the heat sink 30 and working fluid in accordance with disclosure below, without permitting electrically connectivity therebetween.

FIG. 1 shows that a controller 32 receives a patient temperature signal from a temperature sensor 34. In accordance with present principles, the controller 32 accesses a logic module 36 to control the heat sink 30 and pump 20 in accordance with logic set forth further below. The controller 32 may be implemented by any suitable processor. The temperature sensor 34 may be any suitable temperature sensor such as a thermocouple, resistance temperature detector (RTD), tympanic IR sensor, or other sensor that outputs a signal representative of patient temperature, preferably patient spinal temperature. The sensor 34 may be placed in the bloodstream of the patient, or in the esophagus, rectum, bladder, or near the ear canal to sense tympanic temperature, or in the retroperitoneal cavity. The logic module 36 may be implemented in electronic storage such as disk or solid state memory and accessed by a processor to execute the present logic.

Now referring to FIG. 2, a patient 40 has a digestive tract 42 and a spinal column 44 anterior thereto, with a retroperitoneal space 46 formed adjacent the spinal column 44. To cool the spine for, e.g., spinal surgery, or to protect it during hypoxic events such as but not limited to those caused by cardiac arrest, myocardial infarction, stroke, and trauma that causes spinal hypoxia, the catheter 12 is advanced percutaneously into the retroperitoneal space 46 as shown, preferably with the heat exchange element 13 placed near or against the spinal column 44. A sheath may be used for placement. In any case, the catheter 12 does not reside in the vasculature of the patient. Coolant is then circulated through the catheter 12 and coolant temperature is controlled by the controller 32 in response to feedback from the sensor 34 to establish a desired patient temperature, e.g., to establish a physician-defined spinal temperature or core body temperature. While the particular METHOD AND APPARATUS FOR SPINAL COOLING is herein shown and described in detail, it is to be understood that the subject matter which is encompassed by the present invention is limited only by the claims.

What is claimed is:

1. A method for cooling at least a portion of a spinal column of a patient disposed in an operating room, comprising:
    advancing a closed loop heat exchange catheter into the retroperitoneal space of the patient;
    circulating heat exchange fluid through the catheter to cool the retroperitoneal space and thereby cool the spinal column; and
    conducting spinal surgery on the patient.

2. The method of claim 1, wherein the catheter is advanced percutaneously into the patient.

3. The method of claim 1, wherein at least one heat exchange element of the catheter is positioned against the spinal column.

\* \* \* \* \*